(12) United States Patent
Kucukay et al.

(10) Patent No.: US 8,834,944 B2
(45) Date of Patent: Sep. 16, 2014

(54) OINTMENT FOR THE TOPICAL TREATMENT OF HAEMORRHOIDS

(75) Inventors: Feyyaz Kucukay, Istanbul (TR); Mehmet Sait Kucukay, Istanbul (TR)

(73) Assignee: Feyyaz Kucukay, Istanbul (TR)

( * ) Notice: Subject to any disclaimer, the term of this patent is extended or adjusted under 35 U.S.C. 154(b) by 161 days.

(21) Appl. No.: 13/143,428

(22) PCT Filed: Jan. 13, 2009

(86) PCT No.: PCT/EP2009/000148
§ 371 (c)(1),
(2), (4) Date: Jul. 29, 2011

(87) PCT Pub. No.: WO2010/081485
PCT Pub. Date: Jul. 22, 2010

(65) Prior Publication Data
US 2011/0274772 A1 Nov. 10, 2011

(51) Int. Cl.
*A61K 36/52* (2006.01)
*A61K 9/00* (2006.01)
*A61K 36/60* (2006.01)
*A61K 36/28* (2006.01)
*A61K 36/77* (2006.01)

(52) U.S. Cl.
CPC ........... *A61K 9/0031* (2013.01); *A61K 36/52* (2013.01); *A61K 36/60* (2013.01); *A61K 36/28* (2013.01); *A61K 36/77* (2013.01)
USPC ............ 424/771; 424/725; 424/774; 424/776

(58) Field of Classification Search
CPC ..... A61K 36/60; A61K 36/185; A61K 36/28; A61K 36/52; A61K 8/97
USPC .................................. 424/771, 774, 776, 725
See application file for complete search history.

(56) References Cited

U.S. PATENT DOCUMENTS

| | | | |
|---|---|---|---|
| 6,228,387 B1 | 5/2001 | Borod | |
| 6,942,851 B2 * | 9/2005 | Fath et al. | 424/70.1 |
| 2004/0185123 A1 * | 9/2004 | Mazzio et al. | 424/730 |
| 2007/0122496 A1 * | 5/2007 | Managoli | 424/725 |

FOREIGN PATENT DOCUMENTS

| | | | |
|---|---|---|---|
| EP | 0348215 A3 | | 6/1989 |
| EP | 0348215 A2 | | 12/1989 |
| EP | 2022504 A1 | | 2/2009 |
| JP | 2002-265325 A | * | 9/2002 |
| JP | 2003-286183 A | * | 10/2003 |

OTHER PUBLICATIONS

Zhang Zixing et al., "Fig Leaf Decoction for Treatment of Hemorrhoids", Gansu Chinese Traditional Mediciane, Jun. 30, 1992, No. 2, p. 28.
Sun Jialin, "Good Sells of Horse Chestnut Preparatio", Feb. 28, 1986, No. 2, p. 47.
Ma Laibao et al., "Hemorrhoids", Food Theraphy and Health Care Record Among the People, First Edition, Rural Reading Press, Jun. 30, 1998, pp. 139-140.
Office Action and brief translations of rejections from Chinese Patent Application No. 200980154508.4 dated Jul. 26, 2012.
Database WPI Week 200370, Thomson Scientific, London, GB; AN 2003-741839, XP002467171 & KR 2003 014 554 A (Park G R) Feb. 19, 2003, abstract.
Database WPI Week 200231, Thomson Scientific, London, GB; AN 2002-258391 XP002467172 & CN 1 330 931 A (Su L) Jan. 16, 2002, abstract.
Jadeja, B A et al., "Herbal remedies used for haemorrhoids by tribals of Saurashtra, Gujarat", Indian Journal of Traditional Knowledge, vol. 5(3), Jul. 2006, pp. 348-352.
Abascal, Kathy et al., "Botanical Treatments for Hemorrhoids", Alternative & Complementary Therapies, Dec. 2005, pp. 285-289.

* cited by examiner

*Primary Examiner* — Susan Hoffman
(74) *Attorney, Agent, or Firm* — Park, Vaughan, Fleming & Dowler LLP

(57) ABSTRACT

The present invention provides an ointment comprising aqueous extract of fig leaves, horse chestnut, artichoke leaves and walnut shells, for the treatment of hemorrhoids; a method of manufacturing such an ointment; and the use of fig leaves, artichoke leaves or walnut shells for the manufacture of a medicament for the treatment of hemorrhoids. Preferably, the ointment further comprises lanolin and petroleum jelly (Vaseline). Preferably, the method comprises extracting fig leaves, horse chestnut, artichoke leaves and/or walnut shells using heated water, and admixing thereto lanolin and petroleum jelly (Vaseline) so as to result in the ointment. The ointment preferably further comprises 'Huile de Cade'.

2 Claims, 5 Drawing Sheets

OINTMENT FOR THE TOPICAL TREATMENT OF HAEMORRHOIDS

Figure 1:
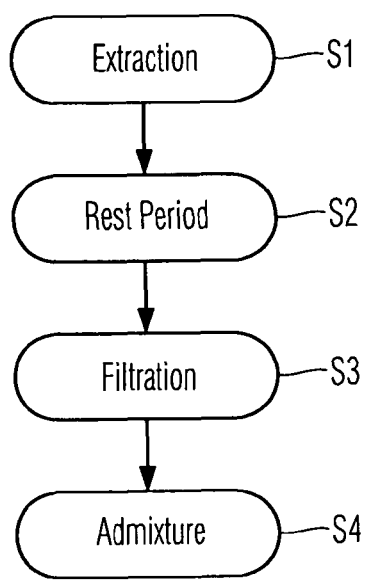

The present invention relates to a composition for the topical treatment of haemorrhoids comprising aqueous extracts of fig leaves, walnut shells and/or artichoke leaves, in particular in combination with aqueous extracts of horse chestnuts. The invention also relates to a method of manufacturing an ointment comprising these ingredients; and to the use of fig leaves, walnut shells and/or artichoke leaves for the manufacture of a medicament for the topical treatment of haemorrhoids.

Conventional compositions have been largely restricted to alleviating the symptoms associated with haemorrhoids but have been found unsatisfactory as regards the healing thereof. For example, international application WO 2004/073757 A1 discloses an anal treatment pad to which a skin care composition comprising zinc oxide, niacinamide and hexamidine are applied. However, even the repeated application of such a composition will not result in a substantial regression of haemorrhoids.

It is an object of the invention to provide a composition, a method for manufacture of a composition, and uses of a composition which may overcome the limitations of the prior art with respect to the healing of haemorrhoids.

The inventor has found that the deficiencies of the conventional composition may, according to a first aspect, be overcome by a composition comprising aqueous extracts of at least three selected from the group consisting of fig leaves, horse chestnut, artichoke leaves and walnut shells. These extracts are active agents and combine synergistically. All four ingredients may, but need not be present. According to another aspect, the invention provides a method for the manufacture of an ointment useful in the treatment of haemorrhoids including extracting the above ingredients with heated water, filtering the mixture, and admixing gelling agents to the filtrate. Also, according to further aspects, the invention provides the use of fig leaves, artichoke leaves or walnut shells for the manufacture of a medicament for the treatment of haemorrhoids.

It has been found that upon several applications of the inventive ointment or medicament, respectively, haemorrhoids will significantly regress and eventually vanish.

In general terms, the present invention comprises the following items:

1. A composition, comprising aqueous extracts of at least three selected from the group consisting of fig leaves, horse chestnut, artichoke leaves and walnut shells, for the treatment of haemorrhoids.
2. The composition according to item 1, further comprising a liquid plant oil.
3. The composition according to item 2, wherein the plant oil comprises Cade Oil.
4. The composition according to item 2 or 3, wherein the plant oil comprises at least one selected from the group consisting of an olive oil extract of balsam apple, storax, and *nigella sativa* oil, or two or all of these.
5. The composition according to one of the preceding items, further comprising lanolin (wool wax) or/and petroleum gelly (Vaseline) as a gelling agent.
6. The composition according to item 5, wherein the composition comprises 20% to 40% by volume of plant oils, 20% to 40% by volume of the gelling agents, and 20% to 40% by volume of the aqueous extracts.
7. Use of fig leaves for the manufacture of a medicament for the treatment of haemorrhoids.
8. Use of artichoke leaves for the manufacture of a medicament for the treatment of haemorrhoids.
9. Use of walnut shells for the manufacture of a medicament for the treatment of haemorrhoids.
10. A method of manufacture of an ointment, comprising:
    extracting (S1) at least three selected from the group comprising fig leaves, horse chestnut, artichoke leaves and walnut shells using heated water;
    filtering (S3) the extract so as to separate its active agents from the solid residue; and
    admixing (S4) a gelling agent to the filtrate so as to result in an ointment.
11. An applicator containing the composition according to one of items 1 to 6, the medicament according to one of items 7 to 9, or the ointment manufactured according to item 10.

According to embodiments of the invention, the composition further comprises a liquid plant oil, in particular cade oil or/and storax or/and an olive oil extract of balsam apples. According to an embodiment, the ointment or medicament, respectively, comprises lanolin or/and petroleum gelly (Vaseline). These gelling agent help in the transport of the active ingredients to the skin by providing an emulsion. According to embodiments, the active agent extract constitutes 20% to 40% by volume, preferably 25% to 35% by volume of the total ointment.

According to an embodiment of the inventive method, the ingredients are batch-wise extracted with water under gentle heating, allowed to stand for completion of the extraction, filtered, and the lanolin or petroleum gelly (Vaseline) admixed to the filtrate.

According to a further embodiment, the heating is carried out with an average temperature increase of not more than 1° C./min, preferably not more than 20° C./h, in particular from 6° C./h to 10° C./h up to boiling, and the mixture is then allowed to cool. In examples, the mixture is then allowed to mature under ambient conditions for at least one week, up to 2 weeks, or for 10 to 12 days. The above heating scheme may avoid local and/or prolonged overheating which may result in reduced activity of some of the ingredients.

Further, the composition in embodiments comprises one or more selected from a second group of assisting agents enhancing the activity of the ingredients of the above first group. In embodiments of the invention, the amount of assisting agent extracts combined is 5% to 15%, or 7% to 12%, or 9% to 10% by volume of the total ointment. On the other hand, the combined amount of the assisting agent extracts is ¼ to ¾ of the combined amount of the active agent extracts.

Further, the composition may comprise one or more selected from a third group of helping agents. In embodiments of the invention, the amount of helping agent extracts combined is 0.5% to 10%, or 1% to 7%, or 2% to 4% by volume of the total ointment. On the other hand, the combined amount of the helping agent extracts may be 10% to 25% of the combined amount of the active agent extracts.

The combined amount (by weight) of assisting agents and helping agents shall not, in embodiments, exceed the amount by weight of the single most abundant ingredient of the first group. Herein, the amounts employed for the extraction are contemplated. In embodiments, the amounts by weight used for the extraction are from about 0.01% to about 10% by weight independently for each ingredient (if present) of the first to third groups, or/and from about 1% to about 30% for the combined total of the ingredients of the first to third groups, based on the amount of water used in the extraction.

In the event a continuous extraction process is employed, the above ratios apply for the respective mass flow rates per unit time.

Further, the composition may comprise one or more selected from a fourth group of chemical agents as desired, which agents will help to extend product shelf-life, durability and longevity, and so are "stabilizers". In embodiments of the invention, the combined amount of stabilizers is 0.1% to 20%, or 1% to 10% by volume of the total ointment. On the other hand, the combined amount of the stabilizers is 1% to 30% by volume of the combined amount of the active agent extracts in some embodiments.

Further, the composition may comprise one or more selected from the group of assisting plant oils as desired. In embodiments of the invention, the combined amount of plant oils is 10% to 50%, or 20% to 40%, or 25% to 35% by volume of the total ointment.

Further, the composition may comprise a local analgetic, such as lidocain, or/and cortisone as desired, to reduce itching or burning which may be caused in sensible persons by some of the active ingredients.

Figure 2:
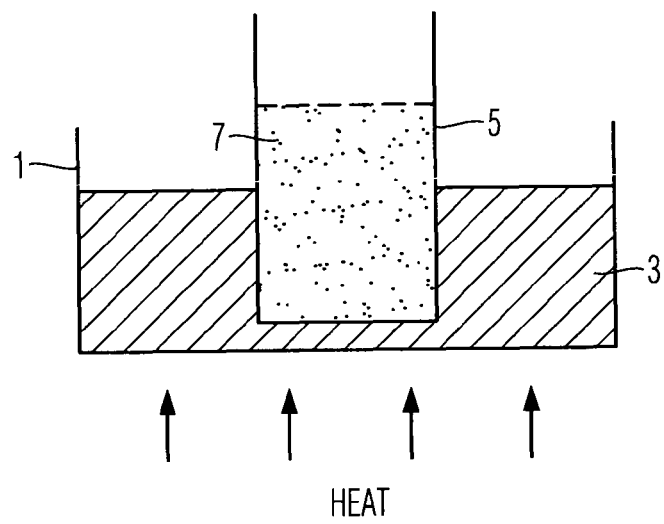
Figure 3:
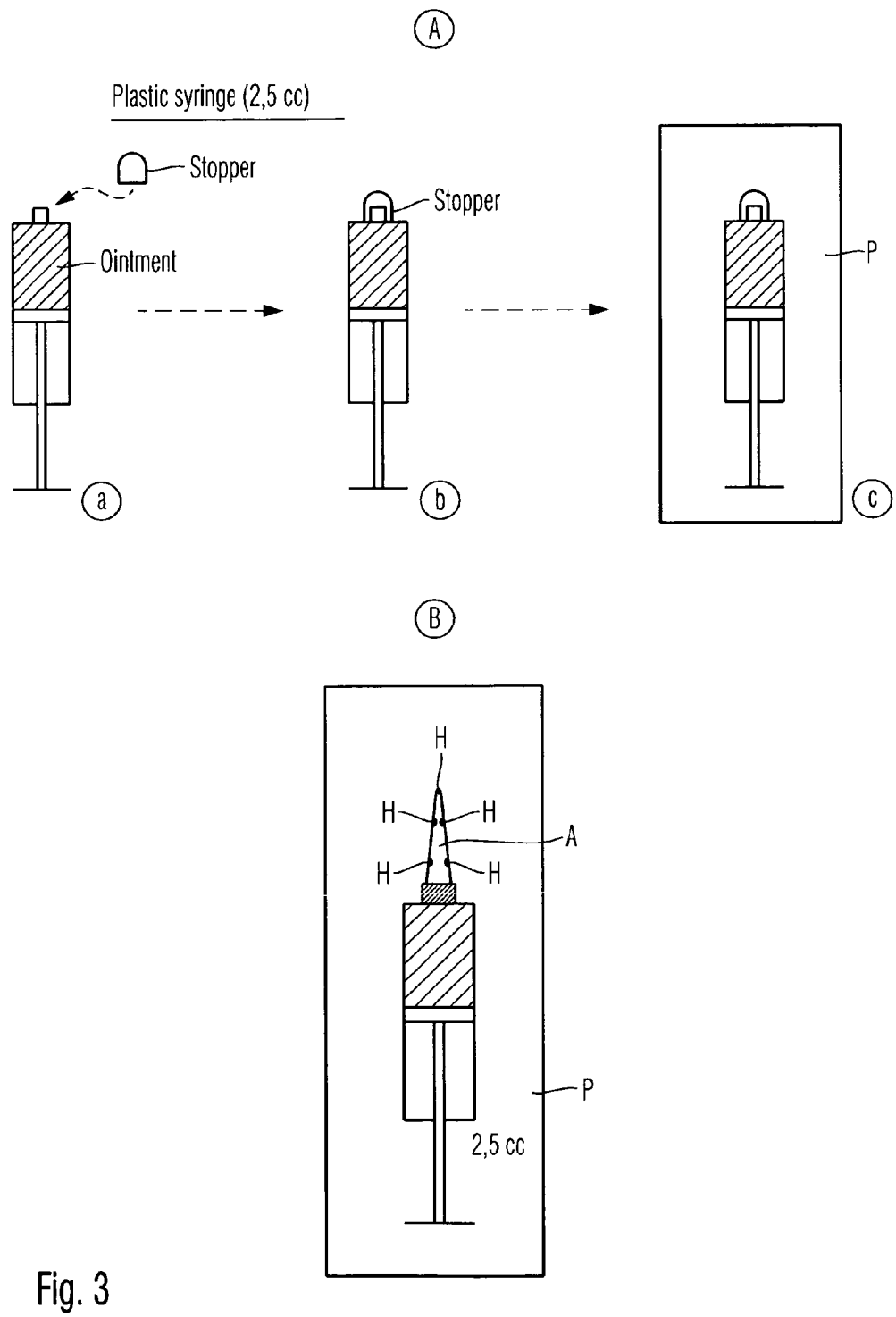
Figure 4A:
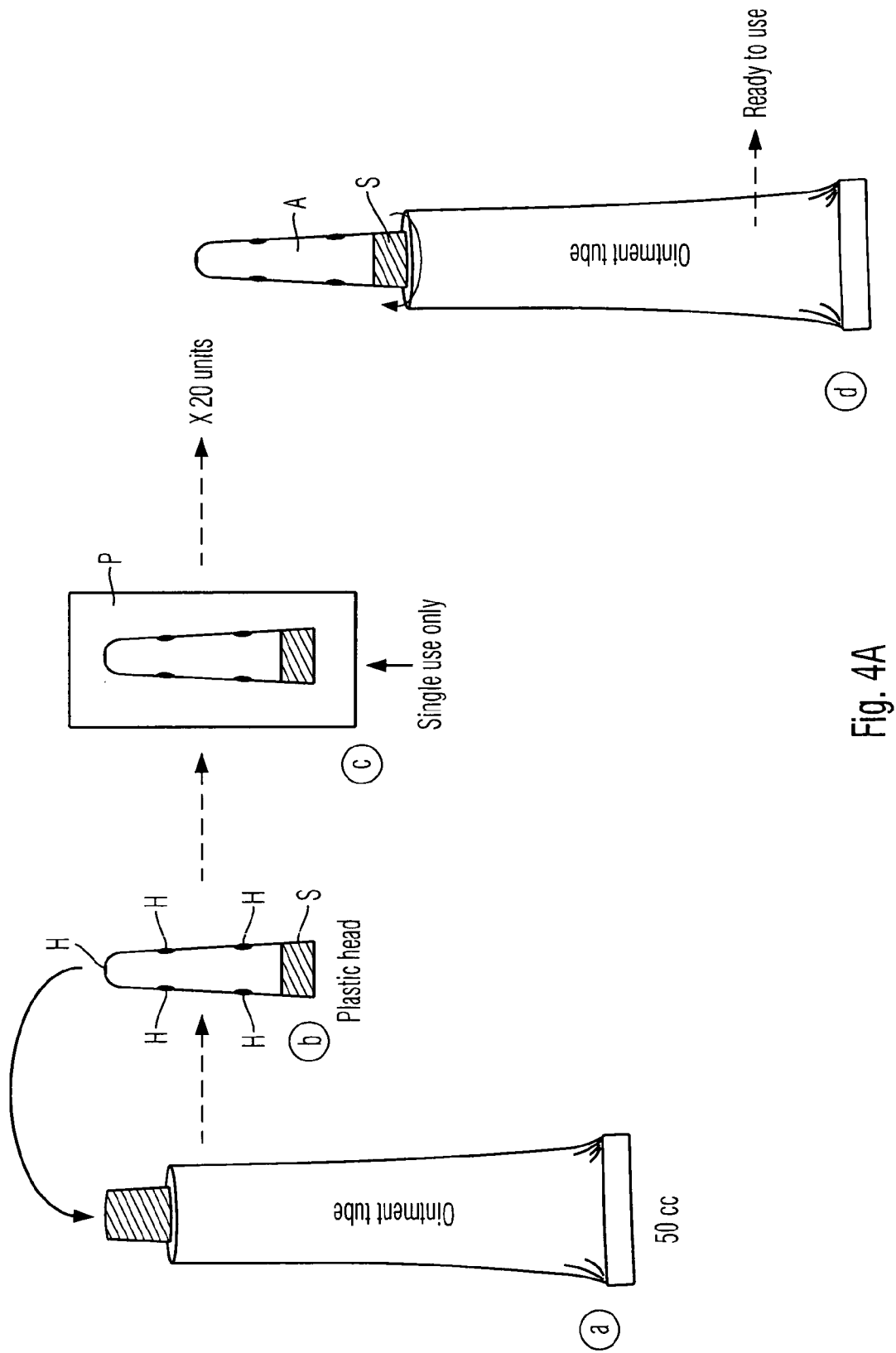
Figure 5:
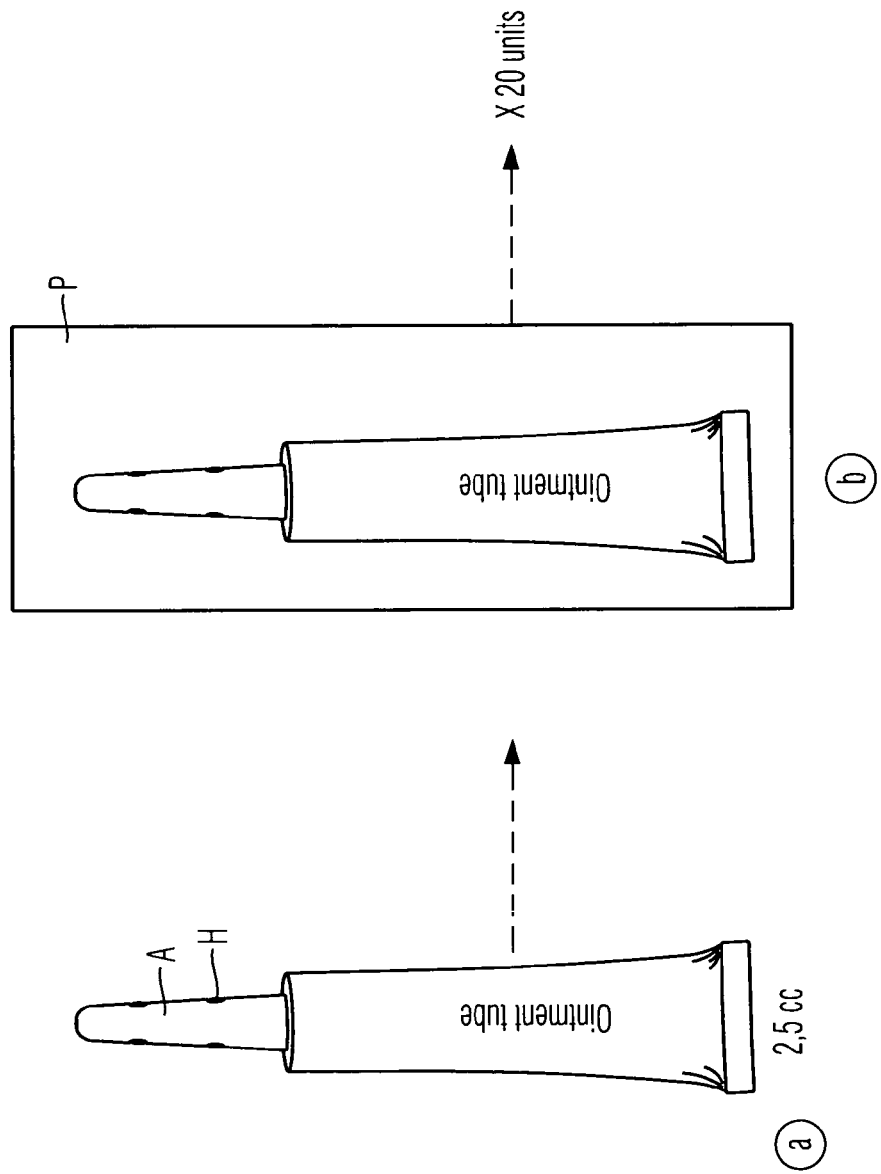

In the following, the invention will be described in detail and in conjunction with the following drawings:

FIG. 1 shows a flow diagram of a method according to the invention;

FIG. 2 schematically shows a bain-de-Marie as employed in a preferred embodiment of the invention;

FIGS. 3A, B schematically show a plastic syringe package as a preferred embodiment of the invention;

FIGS. 4A, B schematically show a combination of a reservoir tube and a set of disposable plastic applicator heads as a preferred embodiment of the invention; and FIG. 5 shows a single application tube as a preferred embodiment of the invention.

Generally, the ointment according to the invention may comprise an aqueous base liquid containing herbal essences; a proportion of vegetable oils; and a proportion of gelling agents. The amount of each of these is most preferably 30% to 33% of the total by volume. Additionally, a minor proportion of preferably 1% to 10% by volume of the total is constituted by stabilizing chemicals. Further, local analgesics and/or cortisone may be added in suitable amounts.

The most active ingredients of the first group are the following: leaves of the fig (*ficus carica*), husks of the walnut (*juglans regia*), leaves of the artichoke (*cynara scolymus*) and the fruits of the horse chestnut (*aesculus hippocastanum*). A preferred proportion of the first group of active ingredients is 30% to 75% by volume, preferably 50% to 70%, more preferably 55% to 65% of the aqueous base liquid.

The second group of assisting ingredients consists of three subgroups: Namely, a first subgroup of very desirable ingredients, consisting of skin of the pomegranate (*punica granatum*), stems and stalks of the aubergine (*solanum melongena*), acorns (*quercus macrolepis*), and pine cones (*pinus strabus*); a second subgroup of somewhat less important ingredients, consisting of cypress cones (*cupressus sempervirens*), juniper berry seeds (*juniperus communis*), oak tree skin (*quercus*), leaves and seeds of nettles (*urtica urens*), myrtle leaves (*myrtus communis*), dragon's blood or sanguis draconis (*dracaena draco*), balsam apple fruits (*momordica charantia*); and a third subgroup of even less important ingredients, from which one or more may desirably be selected, consists of: *nigella sativa, aloe vera*, milfoil (*achillea millefolium*), leaves of quince (*cyclonia vulgaris*), solidago officinalis, ginger (*zingiber officinale*), fennel (*foeniculum vulgare*), rosemary (*rosmarinus officialis*), and cassia (*senna corymbosa*). A preferred proportion of the entire second group of assisting ingredients is 10% to 50% by volume, preferably 20% to 40%, more preferably 25% to 35% of the aqueous base liquid.

The third group of helping ingredients, from which one or more may desirably be selected, consists of: fern leaves, common buckthorn, mallow, *melissa officinalis, acanthus dioscoridis, cichorium endivia*, hawthorn, leek, carob, *ziziphora*, borage, asa foetida, *plantago, sambucus nigra*, buttercup, oleander, coconut skin, mullein, lesser celandine, coriander, arborvitae, anis, flax seed, and *vaccinium myrtillus*. A preferred proportion of the third group of helping ingredients is 1% to 25% by volume, preferably 2% to 20%, more preferably 5% to 15% of the aqueous base liquid.

The group of chemicals, from which one or more may desirably be selected, consists of: Alum ($M^I Al(SO_4)_2$, with $M^I$ representing a monovalent ion such as ammonium or an alkali metal, preferably potassium), boric acid, salicylic acid, zinc oxide, calcium carbonate, sodium benzoate, and a solution of basic aluminum acetate (liquor alumini subacetatis).

It will be understood that the herbal ingredients, and the stabilizing chemicals, may desirably be used in comminuted form e.g. by crushing and/or milling.

The composition further comprises a liquid plant oil, in particular cade oil or/and storax or/and an olive oil extract of balsam apples or/and *nigella sativa* oil. The group of preferable vegetable oils, from which one or more may desirably be selected, further consists of: almond oil, castor oil, sesame oil, olive oil, sunflower oil, hazelnut oil, and cocoa oil. Any one of the vegetable oils may preferably be present in an amount by weight of between 0.0001% to 20% based on the total amount of ointment, preferably in an amount by weight of between 0.001% to 10%. On the other hand, the main proportion is preferably made up of storax oil in an amount of from 5% to 30%, preferably from 10% to 20%, more preferably from 12.5% to 17.5% by volume of the oils. An olive oil extract of balsam apple is preferably contained in an amount of from 2% to 25%, preferably from 5% to 15%, more preferably from 7.5% to 12.5% by volume of the oils. Cade oil is preferably contained in an amount of from 10% to 40%, preferably from 20% to 30%, more preferably from 22.5% to 27.5% by volume of the oils. *Nigella sativa* oil is preferably contained in an amount of from 2% to 25%, preferably from 5% to 15%, more preferably from 7.5% to 12.5% by volume of the oils. Other, less important oils, namely ricine oil, sesame oil, cacao oil and almond are each preferably contained in an amount of from 1% to 25%, preferably from 2% to 15%, more preferably from 5% to 10% by volume of the oils. Sun flower oil and hazelnut oil are each preferably contained in an amount of from 0.1% to 20%, preferably from 1% to 10%, more preferably from 2% to 6% by volume of the oils.

The group of analgetics may also comprise metamizole sodium (Novalgin). Preferably, more of lidocain and less of Novalgin are used, in a ratio of at least 3:2. Lidocain may be used in the form of a 5% solution (such as Jetocain). Moreover, this group comprises substances to alleviate itching such as cortisone. The amounts are preferably selected so as to be pharmaceutically acceptable, yet alleviate unpleasant sensations.

In addition, the composition may desirably comprise natural wax.

A preferred embodiment of the method of preparation will be described in detail in the following:

A big metal pot (volume about 15 to 50 liters) is filled with water. The ingredients of the first and second groups (and, if present, the third group) are put in the water. The water is heated to boiling within 8 to 12 hours (process step S1). After heating and boiling, the heating is turned off and the liquid is left to rest for one to two weeks, preferably for up to days (process step S2). Then, the mixture is filtered (process step S3) and the filtrate is ready for further use as a base liquid.

The amounts by weight used for the extraction are from about 0.1% to about 1% by weight independently for each ingredient (if present) of the first to third groups, or/and from about 5% to about 15% for the combined total of the ingredients of the first to third groups, based on the amount of water used in the extraction.

The vegetable oils are mixed together in a pot until harmonized. Then, the mature preparation is admixed while continuously stirring with the base liquid. The total amount of vegetable oils is preferably from 20% to 40% by volume; more preferably, from 30% to 33% of the total by volume.

The chemicals of the fourth group are also mixed together in a cup with water until harmonized to a slurry. Then, the mature preparation is admixed, while continuously stirring, with the mixture of the base liquid with the vegetable oils. In another embodiment, the stabilizing mixture is added first to the herbal essences, and the oils are admixed thereafter. The total amount of chemicals is preferably from 0.1% to 20% by volume; more preferably, from 1% to 10% of the total by volume.

The gelling agents are gently heated in a water bath (see FIG. 2) so as to become flowable, and then poured slowly into the basic liquid (process step S4). During the addition of lanolin and vaseline, stirring is continued until a creamy consistence is achieved. The preparation is then filled into boxes, tubes or disposable syringes. Herein, the proportion of the lanolin and Vaseline together are preferably less by weight, or from 1:4 to 1:1, preferably from 1:3 to 1:2, than the aqueous liquid, if the ointment is intended to be applied by means of syringes or a treatment pad; and is preferably more by weight, or from 5:2 to 1:1, preferably from 2:1 to 3:2, than the watery phase if intended to be applied directly or by means of a treatment pad. In the latter case, the amount of (anhydrous) lanolin and vaseline together is preferably about as much by weight, or from 2:1 to 1:2, preferably from 3:2 to 2:3, as the aqueous phase. Generally, the mixture preferably comprises, per 1 part of petroleum gelly (Vaseline), 1 to 4 parts, preferably 2 to 3 parts of lanolin (wool wax), and 2 to 7 parts, preferably 3 to 5 parts of the aqueous extracts. It is assumed that when relatively less lanolin and Vaseline are added, the emulsion stays to be of the type oil-in-water and therefore is relatively more creamy in touch; whereas, if relatively more lanolin and/or Vaseline are added, a phase inversion may occur to the water-in-oil type of emulsion, which feels relatively more greasy. Each type may be more advantageous than the other in certain applications. In either case, also solid ingredients may be present. The total amount of gelling agents is preferably from 20% to 40% by volume; more preferably, from 30% to 33% of the total by volume. In proportion to one another, it is preferred that the amount of lanolin is 50% to 90%, preferably 65% to 85%, more preferably 75% to 80% by volume of the gelling agents, whereas the amount of Vaseline is 10% to 50%, preferably 15% to 35%, more preferably 20% to 25% by volume of the gelling agents.

According to a best mode of preparing the ointment, the following steps are carried out in order:

First, the metal pot is filled with water. The herbs and plants of the first, second and third groups are put in the pot and heated within 8 to 12 hours to boiling. After heating and boiling, the liquid is left to rest for 8 to 10 days. Then, the liquid is filtered to provide the base liquid.

Then, in another big pot the vegetable oils are mixed until a homogeneous mixture is achieved. No heating is necessary in this step, but may be applied to accelerate the procedure.

Then, in another pot, the chemicals are admixed with water to provide a slurry. The slurry is continually mixed until an even distribution is achieved. Also in this step, heating is not necessary, but may be applied to accelerate the procedure.

Then, in yet another pot, the analgesics and the cortisone are admixed to homogeneity.

The oils, chemicals slurry and analgesic composition are then admixed to the base liquid until an emulsion is achieved. Now, gently heated lanolin and Vaseline are added to the emulsion until the mixture becomes a mature, creamy liquid. Herein, (anhydrous) lanolin acts to absorb excess water in the watery (oil-in-water) emulsion. Therefore, upon addition of lanolin, the watery emulsion will become a thick cream once a sufficient amount of water is absorbed by lanolin.

The step of heating the gelling agent is explained with reference to FIG. 2: Herein, a metal pot 1 is filled with water 3, to which heat is applied. A plastic package 5 is suspended into the water, which plastic package is filled with the gelling agents 7. In this manner, the viscosity of the gelling agents is gradually lowered, until their flowability is sufficient to allow forming the emulsion as explained above.

For applying the ointment, the following methods are contemplated: The ointment may be applied directly with a finger to the affected portion of the anus. Or, the ointment may be applied to a treatment pad, which may be worn under the garment. Moreover, the ointment, particularly if prepared with relatively less lanolin and Vaseline and therefor less viscous, may be drawn into a disposable plastic syringe (without the needle) and applied by slowly moving the plunger of the syringe the opening of which is held near the affected areas.

When applying the ointment directly with a finger, it may be preferable to use a disposable plastic finger cover. When using a syringe, there are two embodiments: In the first embodiment (FIG. 3A), the outlet of the syringe is sealed (a, b) with a removable stopper. In the second embodiment (FIG. 3B), the syringe carries an applicator tube A with plural holes H, through which the ointment is simultaneously applied to spaced apart locations in the anus. In both embodiments (c), the filled syringe may be packaged P and sealed under inert gas or vacuum. Herein, the ointment content of the syringe is 2.5 cm$^3$.

Figure 4B:
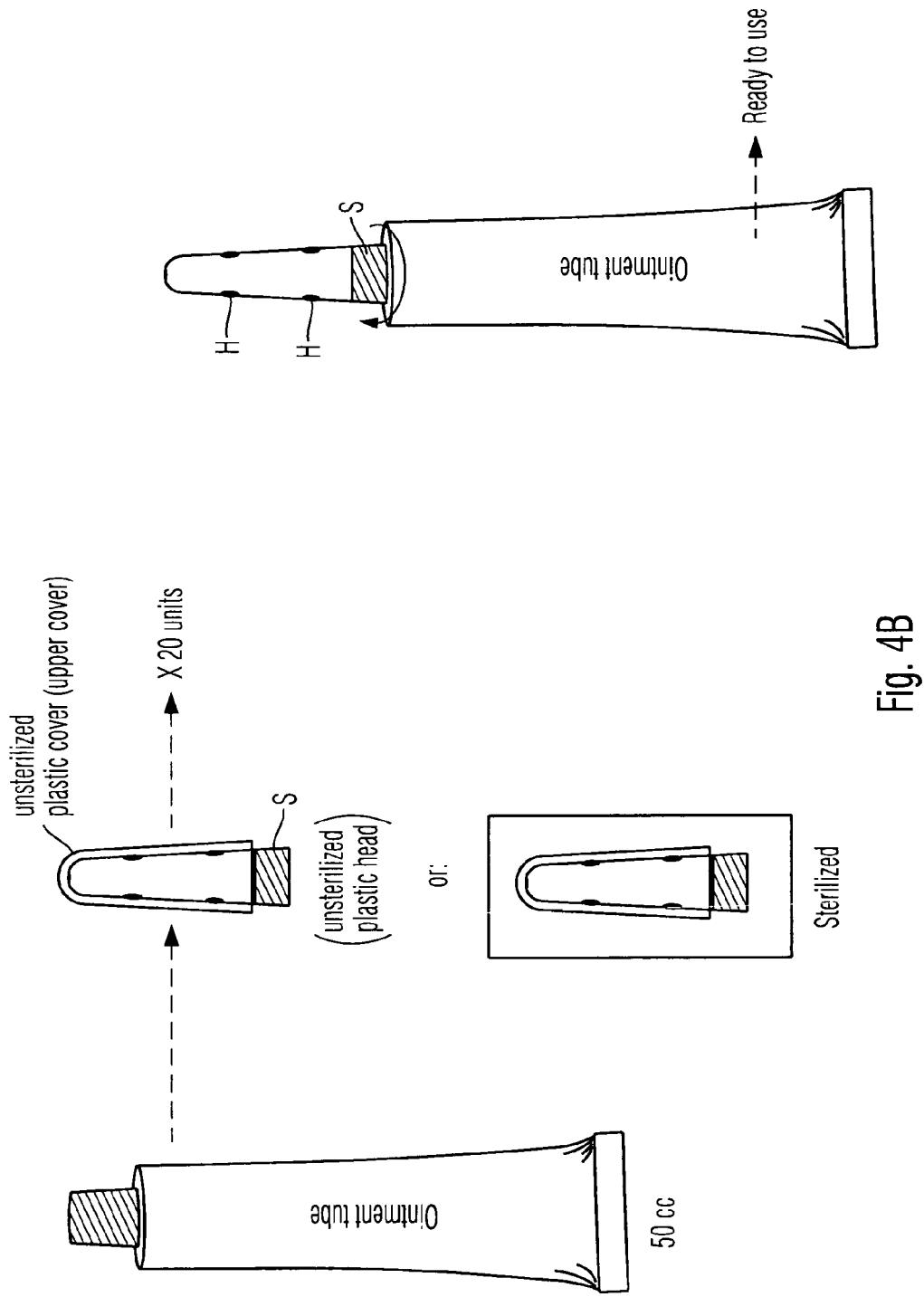

In another embodiment, a reservoir tube of e.g. 50 cm$^3$ contents is contemplated. Again, an applicator tube A having plural holes H is provided, which may be screwed S on the reservoir tube. A set of applicator heads may comprise, e.g., 20 such heads, in a sterilized package P (see FIG. 4A). Additionally, there may be provided an outer plastic cover (see FIG. 4B), which may be sterilized or not. The reservoir tube (containing 20 or so doses) itself may be made of metal or plastic.

In another embodiment, single use tubes of e.g. 2.5 ml ointment content each are packaged P in sets of 20. These small tubes each carry an applicator tube A with plural holes H, as depicted in FIG. 5.

It is contemplated to provide tubes (FIGS. 4A,B and FIG. 5) or boxes filled with the ointment; treatment pads comprising the ointment; or prefilled applicators such as disposable syringes (FIGS. 3A,B). Either of these may be packaged with a gas-tight sealing, under vacuum or inert gas. Herein, the use of additional pads worn between the body and the underwear has the advantage that possible staining of the underwear due to the partly coloured herbal essences may be avoided.

The actual treatment of haemorrhoids, for which the present invention is helpful, includes a twice-daily application of the ointment to the anus (inside and peripherally). It is preferable to apply the ointment once in the morning, after defecation, and once again directly before going to sleep. In a preferred embodiment, a package contains about 20 disposable syringes or collapsible tubes with elongated ejector ducts as applicators, each containing 2 to 3 ml, preferably 2.5 ml of the ointment, sufficient for about 10 days of treatment. Assuming that one package of the ointment contains about 50 cm$^3$ as in FIG. 4, according to the degree (I-IV) of the haemorrhoids, one to four packages will have to be consumed. The degree (I-IV) of haemorrhoids may be defined in the following.

There are two kinds of haemorrhoids, namely inside (internal) haemorrhoids, the symptoms of which are bleeding, pain, and distensibility; and outside (external) haemorrhoids, the symptoms of which, in the first stage (degree I), are burning and itching. In a second stage (degree II), the haemorrhoids may come out during defecation, and slip back by themselves thereafter. In a third stage (degree III), the haemorrhoids have to be pushed back inside after defecation. In a fourth, most severe stage (degree IV), the haemorrhoids remain outside, and it is no longer possible to push them back inside.

In order to assist the treatment, it is desirable that the patient should not suffer from constipation. It is preferable that, accompanying the treatment, the patient mainly consumes fibrous nourishments such as fruit and vegetables. It is further helpful if the patient consumes dry foods, particularly leguminous plants, and at least 1.5 l of water daily. Particularly preferable is a diet containing fresh or dried apricots, fresh or dried plums, flax seed, yogurt, and/or cherries. Preferable beverages include herbal teas (chamomilla, peppermint, thyme, sage, linden and cassia) and a heated mixture of milk, honey and grilled flax seed, the latter in particular at bedtime.

The following foods and beverages should be avoided to assist the treatment: beer, wine, any kind of tinned food, black tea and coffee, any kind of roasted or fried food, tomatoes and tomato sauce or ketchup, pickles, oranges, strawberries, grapes, melons, pepper. Physical activities like walking are recommended, while siting for prolonged times should be avoided.

Although the invention has been explained in the above by reference to specific examples, the invention is to be understood as limited only by the appended claims.

The invention claimed is:

1. A haemorroid-treatment ointment, comprising:
   aqueous extracts of *ficus carica* leaves, horse chestnuts, artichoke leaves, and walnut shells, wherein the extracts are water based; and
   lanolin and/or petroleum jelly as a gelling agent.

2. The haemorroid-treatment ointment according to claim 1, wherein the composition further comprises 20% to 40% by volume of plant oils, 20% to 40% by volume of the gelling agents, and 20% to 40% by volume of the aqueous extracts.

* * * * *